United States Patent [19]

Bargigia et al.

[11] Patent Number: 4,955,726
[45] Date of Patent: Sep. 11, 1990

[54] PERFLUOROPOLYETHERS USED AS FLUIDS FOR TESTING IN ELECTRONIC FIELD

[75] Inventors: Gianangelo Bargigia; Gerardo Caporiccio; Claudio Tonelli; Luciano Flabbi; Giuseppe Marchionni, all of Milan, Italy

[73] Assignee: Montedison S.p.A., Milan, Italy

[21] Appl. No.: 195,356

[22] Filed: May 16, 1988

Related U.S. Application Data

[63] Continuation of Ser. No. 854,785, Apr. 23, 1986, abandoned.

[30] Foreign Application Priority Data

Apr. 24, 1985 [IT] Italy ............................. 20477 A/85

[51] Int. Cl.$^5$ ............................................. G01N 25/00
[52] U.S. Cl. ......................................... 374/57; 165/61; 252/54; 568/615; 568/683
[58] Field of Search ..................... 252/54, 58; 436/3; 568/615, 683; 374/45, 57; 165/61

[56] References Cited

U.S. PATENT DOCUMENTS

| | | | |
|---|---|---|---|
| 3,214,478 | 10/1965 | Milian | 252/580 X |
| 3,242,218 | 3/1966 | Miller | 568/683 X |
| 3,665,041 | 5/1972 | Sianesi et al. | 568/601 |
| 4,523,039 | 6/1985 | Lagow et al. | 568/683 X |

FOREIGN PATENT DOCUMENTS 148482 7/1985 European Pat. Off. .
1226566 3/1971 United Kingdom .

*Primary Examiner*—Robert J. Warden
*Assistant Examiner*—Lyle Alfandary-Alexander
*Attorney, Agent, or Firm*—Stevens, Davis, Miller & Mosher

[57] ABSTRACT

Perfluoropolyethers having an average molecular weight higher than 390 and respectively having a kinematic viscosity lower than 8.5 cSt (at 20° C.), and such as to distill by not more than 10% at temperatures lower than 140° C., and by at least 90% at temperatures not higher than 260° C., or, in the case in which the perfluoropolyether does not contain $CF(CF_3)CF_2O$ units, having a viscosity lower than 18 cSt (at 20° C.), and such as to distill by not more than 10% at temperatures lower than 140° C., and by at least 90% at temperatures not higher than 280° C., are used as the only high-temperature and low-temperature working fluid in the Thermal Shock Tests to which the electronic components are submitted, and at the same time are advantageously used in other tests used in the electronic industry, such as the Gross Leak Test and the Burn in Test, allowing the operators in this field to use one single fluid for a whole set of uses.

1 Claim, No Drawings

PERFLUOROPOLYETHERS USED AS FLUIDS FOR TESTING IN ELECTRONIC FIELD

This application is a continuation of application Ser. No. 854,785, filed Apr. 23, 1986, now abandoned.

BACKGROUND OF THE INVENTION

1. Field of the Invention

The present invention relates to the use of fluids having perfluoropolyether structure as testing media in the electronic industry.

More particularly, the invention relates to the use of such perfluoropolyethers for the Thermal Shock Test (TST), which is described hereinunder.

A further object of the invention is the use of said perfluoropolyethers also for other tests the electronic circuits must commonly undergo, such as the Gross Leak Test and the Burn in Test, which too are described in the following.

2. Description of the Prior Art

The Thermal Shock Test (TST), the modalities of which are described in US MIL STD 883-1105,1 consists in submitting the electronic components to high and low temperature thermal cycles, subsequently testing both the physical characteristics of the materials, and their electrical functional characteristics.

In practice, the components are alternatively and repeatedly dipped into a hot inert fluid, and into a cold inert fluid. The temperatures at which the tests are usually carried out depend on the reliability degree required to the electronic components. The most suitable temperature couples are:
−55° and +125° C.; −65° and +150° C.; −65° and +200° C.; in these cases, temperature excursions of +10° C. for the hot bathes and of −10° C. for the cold bathes are allowed.

It is required that the transfer of the electronic devices from the one to the other bath and vice-versa takes place within very short times, not longer than 10 seconds.

For this test, highly fluorinated fluids are commonly used. It is known in fact that the compounds having a high fluorine content show an exceptionally favourable combination of excellent characteristics, such as the chemical inertia, the thermal stability, the non-flammability, the high electrical resistivity, the low surface tension, the poor solubility in water, the compatibility with many materials, such as elastomers, plastomers and metals.

Perfluoroalkanes having linear or cyclic structure obtained by fluorinating aliphatic, cycloaliphatic or aromatic hydrocarbons are known. An example representative of the cyclic compounds is perfluorodimethylcyclohexane, obtained by reacting xylene with $CoF_3$.

However, the so obtained fluids are not completely fluorinated, because they contain byproducts still having hydrogen atoms. The presence of such byproducts decreases the thermal stability and the chemical inertia of such fluorinated fluids, limiting their application field.

Moreover, even when these fluids are completely fluorinated, they have not very high boiling temperatures when their pour points are very low.

By "pour point" the temperature is meant at which the liquid, upon cooling, modifies its physical characteristics, i.e., at which its flowing capability decreases, because its viscosity increase. In general, as the pour point the temperature is considered at which the viscosity reaches the value of 100,000 cSt (ASTM D 97 Standard).

For example, for pour points of −70° C. the boiling temperature is at the most of the order of 100° C., whilst the products having higher boiling temperature, of the order of 210° C., suffer from the disadvantage of having too high pour points, of the order of −20° C.

Also perfluorinated compounds having ether or aminic structure, obtained by electrofluorination in hydrofluoric acid of the corresponding hydrogenated compound are known. An example representative of these compounds is perfluorotributylamine.

In this case too, the fluids which are obtained are not completely fluorinated, as it occurs for the above described fluids, and show the same disadvantages.

In Table 1, the physical characteristics of some of the hereinabove mentioned products are reported.

TABLE 1

| Product | Boiling point T° C. | Pour point T° C. |
|---|---|---|
| Perfluorotributylamine | 174 | −50 |
| Perfluorotripentylamine | 215 | −25 |
| Mixture of cyclic ethers of formula $C_8F_{16}O$ | 97 | −110 |
| Perfluorodimethylcyclohexane | 102 | −70 |

It can be seen that a group of these products can be used only at high temperatures, whilst another group can be used only at low temperatures. In fact, the range from the boiling temperature and the pourpoint is generally relatively wide, but not wide enough to enable the same perfluorinated compound to be used both at high and low temperatures.

The compounds belonging to the class of the amines, when have rather high boiling points, have high pour points; the class of cyclic ethers has pour point which can be also very low, but the respective boiling temperatures are low.

The use of couples of different fluids for the low and the high temperatures in the TST implies problem of both practical and economic character.

In practice, the rapid transfer of the pieces being tested from the cold to the hot bath and vice-versa, because of the dragging of the fluids, causes: (1) mutual pollution of the baths, with consequent change of the physical-chemical characteristics of the fluids; (2) loss by evaporation of aliquots, which can also be substantial, of the low-boiling fluid, when this is dragged into the high-temperature tank and when the hot pieces are dipped into the cold bath; (3) increase of the viscosity of the low-boiling fluid polluted by the high-boiling fluid; (4) contemporaneous lowering of the level of the cold fluid, and increase of that of the hot fluid (actually, it occurs a greater dragging of the cold fluid, which is very viscous under the use conditions); (5) need for the equipment to be stopped from time to time to replace the fluids; (6) need for a rectifier unit to be available for the reclaiming of the two mutually polluted fluids.

The demand hence existed for a fluid suitable to be individually used both at high and low temperatures, so as to avoid the above described drawbacks, and such to be used also for other tests of electronic industry, such as Gross Leak Test and Burn in Test.

THE PRESENT INVENTION

The object of the present invention is hence to provide a fluid for use in the TST as the only fluid for both high and low temperatures, which fulfills the requisite of chemical inertia and which at the same time has high boiling temperature, higher than the temperature at which the test is carried out, and good fluidity at low temperatures, as evidenced by the pour point.

A further object of the present invention is to provide a fluid which, besides being suitable for use in the TST, can be used also for other tests used in the electronic industry, e.g., the Gross Leak Test (MIL 883C-1014) and the Burn in Test, hereinunder described, enabling the operators in this field to use one fluid only for all these uses.

The object of the invention are hence fluids having perfluoropolyether structure, selected from the following classes of compounds, comprising the structural units of the following type:

(1) (CF(CF$_3$)CF$_2$O) and (CFXO) randomly distributed along the perfluoropolyether chain, wherein X is equal to —F, —CF$_3$;
(2) (CF(CF$_3$)CF$_2$O);
(3) (CF(CF$_3$)CF$_2$O), this class comprises furthermore the characteristic group —CF(CF$_3$)—CF(CF$_3$)—;
(4) (CF(CF$_3$)CF$_2$O), (C$_2$F$_4$O), (CFXO) randomly distributed along the perfluoropolyether chain, wherein X is equal to —F, —CF$_3$;
(5) (C$_2$F$_4$O), (CF$_2$O) randomly distributed along the perfluoropolyether chain;
(6) (CF$_2$CF$_2$CF$_2$O);
(7) (C$_2$F$_4$O);

and characterized by having an average molecular weight of at least 390, kinematic viscosity lower than 8.5 cSt (at 20° C.) and such as to distill under atmospheric pressure by not more than 10% at temperatures lower than 140° C. and by at least 90% at temperatures not higher than 260° C., or, in the case in which the perfluoropolyether does not contain CF(CF$_3$)CF$_2$O units, having viscosity lower than 18 cSt (at 20° C.) and such as to distill by not more than 10% at temperatures lower than 140° C. any by at least 90% at temperatures not higher than 280° C.

Perfluoropolyethers having viscosity lower than 6 cSt (at 20° C.) with 10–90% distillation range comprised between 150° and 230° C., or having viscosity lower than 10 cSt (at 20° C.) with 10–90% distillation range comprised 150° and 250° C., for perfluoropolyethers not comprising CF(CF$_3$)CF$_2$O units, are preferred.

The viscosity, in the present invention, is always measured at 20° C.

The perfluoropolyethers containing the indicated units are known, and are preferably selected among the following classes:

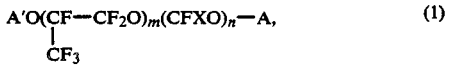
(1)

wherein X is equal to —F, —CF$_3$; A and A', equal to or different from each other, can be —CF$_3$, —C$_2$F$_5$, —C$_3$F$_7$; the units CF(CF$_3$)CF$_2$O and CFXO are randomly distributed along the perfluoropolyether chain, m and n are integers, n can be zero, and the m/n ratio is $\geq 2$ when n$\neq$0 and is such that the viscosity is lower than the hereinabove indicated value of 8.5 cSt.

These perfluoropolyethers are obtained by the reaction of hexafluoropropene photooxidation according to the process as disclosed in UK Patent No. 1,104,482 and subsequent conversion of the end groups into chemically inert groups, according to as disclosed in U.K. Patent No. 1,226,566;

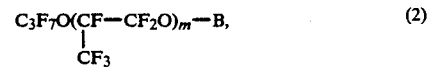
(2)

wherein B can be —C$_2$F$_5$, —C$_3$F$_7$, and m is a positive integer, and such that the viscosity of the product is lower than the hereinabove indicated value of 8.5 cSt.

These compounds are prepared by ionic oligomerization of hexafluoropropene epoxide and subsequent treatment of the acyl fluoride (—COF) with fluorine, according to the processes as disclosed in U.S. Pat. No. 3,242,218;

(3)

wherein m is such a positive integer that the viscosity of the product is lower than the hereinabove indicated value of 8.5 cSt.

These products are obtained by ionic telomerization of hexafluoropropene epoxide and subsequent photochemical dimerization of the acyl fluoride, according to processes as disclosed in U.S. Pat. No. 3,214,478;

(4) A'O[CF(CF$_3$CF$_2$O]$_m$(C$_2$F$_4$O)$_n$(CFXO)$_q$—A, wherein A and A', equal to or different from each other, can be —CF$_3$, —C$_2$F$_5$, —C$_3$F$_7$; X is —F, —CF$_3$; m, n and q are integers and can be also equal to zero, but in any case such that the average molecular weight is at least 390 and the viscosity is within the limit as indicated above (8.5 cSt).

These products are prepared by photooxidation of mixtures of C$_3$F$_6$ and C$_2$F$_4$ and subsequent treatment with fluorine according to the process as disclosed in U.S. Pat. No. 3,665,041;

(5) CF$_3$O(C$_2$F$_4$O)$_p$(CF$_2$O)$_q$—CF$_3$, wherein p and q are integers equal to or different from each other, wherein the p/q ratio is comprised between 0.5 and 2, and such that the viscosity is within the limit as indicated (18 cSt). These perfluoropolyethers are prepared according to as disclosed in U.S. Pat. No. 3,715,378, subsequently treated with fluorine according to U.S. Pat. No. 3,665,041;

(6) AO—(CF$_2$CF$_2$CF$_2$O)$_m$—A', wherein A and A', equal to or different from each other, can be —CF$_3$, —C$_2$F$_5$, —C$_3$F$_7$, and m is an integer such that the viscosity of the product is lower than the hereinabove indicated value of 18 cSt.

These products are obtained according to European Patent Application EP No. 148,482;

(7) DO—(CF$_2$CF$_2$O)$_r$—D', wherein D and D', equal to or different from each other, can be —CF$_3$, —C$_2$F$_5$, and r is an integer such that the viscosity of the product is lower than the hereinabove indicated value of 18 cSt.

These products are obtained according to U.S. Pat. No. 4,523,039.

The fluids of the present invention show the characteristic of having a narrow molecular weight distribution, with both the highly volatile and the high-boiling fractions being absent.

Moreover such fluids, by being contemporaneously characterized by a low pour point, show an enough low viscosity for use also at the indicated very low temperatures.

A further characteristic of the fluids of the invention is their volatility; particularly in the case of viscosity less than 4 cSt, the removal by evaporation from the components is easily obtained at the end of the test, so that the tested component can be used with no need for it to be subsequently washed from the residues of the fluid used in the test.

In the case of viscosity greater than 4 cSt it is preferred a washing with chlorofluorocarbon solvents, for example Algofrene 113 ®, in order to remove any residue of the testing fluid from the component.

The contemporaneous presence of these properties in one single fluid makes this class of products particularly suitable for use in the TST; however, they can be also used in other tests used in the electronic industry, and hereindunder described.

The Gross Leak Test, used for the testing of airtight electronic components, is used to evidence possible tightness faults. It consists in dipping for 30 seconds the component into an inert fluid kept at $125° \pm 5°$ C.

The tightness lack is evidenced by the evolution of air bubbles.

According to an improvement of the method, the test pieces are introduced into a closed chamber which is evacuated (pressure $\leq 5$ torr) for 1 hour, so as to remove air from all cavities. With the vacuum being always maintained, a low-boiling fluorinated fluid (e.g., perfluoroheptane) is then introduced, so as to cover the integrated circuits, and the pressure on the liquid is increased up to 5.2 abs.atm., so to cause it to penetrate the possibly present cavities. The pressure is maintained for at least two hours, the test piece is then removed from the chamber, is dried in air and dipped into the fluid at 125° C. Also in this case, the evolution of bubbles is an indication of cavities.

The Burn in Test is used it too to the purpose of evidencing defects as for the useful life of electronic components. It consists in keeping in function for a prefixed time the component kept dipped in an inert fluid heated according to a well defined temperature increase rate or at a well defined temperature comprised within the range of from 150° to 200° C. The circuits not passing this test, and which under normal use conditions would anyway have a short life, are thus rejected.

Further object of the invention is the use, in the case of Burn in test, of perfluoropolyethers having viscosity higher than those indicated hereinabove.

By this way the test can be carried out also at very high temperatures without decomposition and/or evaporation loss of perfluoropolyethers. Particularly, for testing temperatures higher than 200° C. it is preferred to use perfluoropolyethers (PFPE) having viscosity higher than or equal to 8.5 cSt and, in the case PFPE does not comprise $CF(CF_3)CF_2O$ units, higher than or equal to 18 cSt, anyway lower than 200 cSt, preferably lower than 50 cSt.

The following Examples are given to the only purpose of illustrating the invention, and are not to be intended as limitative thereof.

EXAMPLE 1

Two stainless steel tanks A and B of 20 liters of capacity, the temperature of which can be controlled at temperatures respectively higher (tank A) and lower (tank B) than room temperature are prepared.

Into the two tanks 24.1 kg and 36.7 kg are respectively introduced of a perfluoropolyethers mixture of general formula:

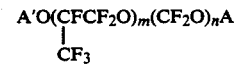

which, on the basis of the N.M.R. data of $^{19}F$, results to have an m/n ratio=3.8 and $A=A'=CF_3$, with minimum amounts of $C_3F_7$ and $C_2F_5$ end groups.

The average molecular weight, determined by the VPO (Vapour Pressure Osmometry) procedure, results to be 480.

The perfluoropolyether has kinematic viscosity $\eta=2.2$ cSt (at 20° C.), a distillation range according to ASTM 1078 method of 161° C.–211° C., pour point −90° C., and specific gravity 1.79 g/ml at 20° C.

A temperature of +125° C., reached within 25 minutes, is selected for the tank A, and of −55° C., reached within 55 minutes, is selected for the tank B.

By using a basket, into the two tanks a set of chip carriers with plastic container and a set of resistors coated with ceramic material are alternatively introduced.

The whole cycle lasts 60 seconds, the total of the permanence time within each tank plus the transfer time being 30 seconds.

After 100 cycles the two tanks contain 26.6 kg and 32.8 kg of fluid respectively.

The most of the missing fluid is found on the working desk between the two tanks; 0.6 kg thereof are recovered, so that the total evaporation loss is not higher than 1.3% by weight.

At the end of the tests the fluid appears unchanged, nor residues are found either in the fluid or in the heat exchange coils or elsewhere.

EXAMPLE 2

The test is carried out as described in Example 1, and using the same fluid, with the difference that the permanence time of the devices being tested inside the cold tank is increased to 90 seconds and the number of cycles is reduced to 20.

It is observed that the temperature fluctuations reach the value of 1° C. in the hot tank, and of 8° C. in the cold tank.

Similarly to what observed in Example 1, neither the formation of residues nor alterations of the fluid are seen.

EXAMPLE 3

The test is carried out as described in Example 1, using a fluid having the same general formula as hereinabove described under point (1), and with the same m/n ratio, but characterized by having average molecular weight 490, viscosity $\eta=2.38$ cSt (at 20° C.), 10–90% distillation range of 162°–218° C., specific gravity 1.80 g/ml, with the difference that the temperature of the fluid is respectively controlled at −65° and +150° C., and that the number of cycles becomes 25 and the permanence time is of 90 seconds and 30 seconds respectively.

It is observed that the temperature of the cold bath fluctuates between −65° C. and −74.8° C., and that the perfluoropolyether remains however fluid enough not to create problems.

During the execution of the test, the level of fluid in tank A increases by 2 cm, due to the effect of cold fluid dragging by the basket containing the chip carriers. No appreciable evaporation losses of fluid from the high-temperature tank are observed.

EXAMPLE 4

By using the same system of tanks as described in Example 1, with the difference that they are interconnected by a level pipe, so that the fluid can freely move between the two tanks, and bringing at constant temperature respectively at −65° C. and +150° C., 100 cycles with permanence times of 30 seconds in each tank are carried out, with no inconvenients.

No temperature fluctuations are observed in the high-temperature bath, whilst in the cold bath the temperature fluctuations are not higher than 5° C. No appreciable fluid losses due to evaporation are observed.

EXAMPLE 5

An equipment similar to that of Example 1 is used, but with 5 liter tanks, each equipped with 2 thermocouples for reading the temperature at two diametrically opposite sites, filled with the same polyether as of Example 3.

The tanks are brought at constant temperature respectively at +125° C. and at −55° C., and two test series, of 40 cycles each, with permanence time of 5 minutes in the high-temperature bath, and of 5 minutes in the cold bath are carried out by exactly following the operative conditions as under MIL 883C, Method 1011.5 Standard.

The temperature fluctuations are of the order of about 3° C. for the cold bath, and of about 1° C. for the hot bath.

Inside the hot bath the thermocouples never signal mutual temperature differences higher than 0.1° C., and in the cold bath such differences never exceed 0.8° C.

At the end of the test, it is observed that the level in the high-temperature tank has increased from 9.9 to 10 cm (as measured at 125° C.), whilst in the other tank it has decreased from 8.6 to 8 cm (as measured at −55° C.).

The increase of fluid volume is of 50 ml in the hot tank, and the loss of fluid from the cold tank is of 350 ml, the most of which is collected on the work desk between the two tanks.

EXAMPLE 6

A cylindrical glass container of 20 cm in diameter, which can be heated by an electrical plate and diametrically crossed by a light beam is filled with a fluid of formula $$CF_3O(C_2F_4O)_p(CF_2O)_qCF_3,$$

having viscosity $\eta = 1.3$ cSt (at 20° C.) and pour point $= -110°$ C. and such as to distill by 90% under 240° C.

The whole is kept at constant temperature at 125° C. and some airtight ceramic integrated circuits (packages), which had already resulted faulty under the same Gross Leak Test as carried out with a fluid available from the market (perfluorotributylamine) are introduced.

After a few seconds, the faults are evidenced as fine bubbles.

The fluid, kept six months under the test conditions, does not show any signs of decomposition or of any kind of alteration.

EXAMPLE 7

With the same equipment, and adopting the same procedure as of Example 6, the Gross Leak Test is repeated on the airtight circuits, using the fluid as of Example 1, characterized by having viscosity $\eta = 2.2$ (at 20° C.), having pour point $= -90°$ C. and such as to distill by 90% under 211° C. (ASTM 1708).

The tests proceed regularly without any inconvenients whatsoever.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Method for carrying out Thermal Shock Tests which comprises:

(A) dipping the sample into a liquid perfluoropolyether having a molecular weight of at least 390, at a temperature between −75° and −55° C., and wherein said liquid is selected from the group consisting of the following seven classes:

$$A'O(CF-CF_2O)_m(CFXO)_n-A, \quad (1)$$
$$\underset{CF_3}{|}$$

wherein X is equal to —F or —CF$_3$; A and A', equal to or different from each other, are —CF$_3$, —C$_2$F$_5$ or —C$_3$F$_7$; the units CF(CF$_3$)CF$_2$O and CFXO are randomly distributed along the perfluoropolyether chain, m and n are integers, n being 0 or greater, and the m/n ratio being 2 when n≠0;

$$C_3F_7O(CF-CF_2O)_m-B, \quad (2)$$
$$\underset{CF_3}{|}$$

wherein B is —C$_2$F$_5$ or —C$_3$F$_7$, and m is a positive integer;

$$[C_3F_7O(CF-CF_2O)_m-CF(CF_3)-]_2, \quad (3)$$
$$\underset{CF_3}{|}$$

wherein m is a positive integer $$A'O[CF(CF_3)CF_2O]_m(C_2F_4O)_n(CFXO)_q-A \quad (4)$$

wherein A and A', equal to or different from each other, are —CF$_3$, —C$_2$F$_5$ or —C$_3$F$_7$; X is —F or CF$_3$; and m, n and q are integers;

$$CF_3O(C_2F_4O)_p(CF_2O)_q-CF_3 \quad (5)$$

wherein p and q are integers equal to or different from each other, wherein the p/q ratio is between 0.5 and 2;

AO—(CF$_2$CF$_2$CF$_2$O)$_m$—A'  (6)

wherein A and A', equal to or different from each other, are —CF$_3$, —C$_2$F$_5$ or —C$_3$F$_7$, and m is an integer; and DO—(CF$_2$CF$_2$O)$_r$—D'  (7)

wherein D and D', equal to or different from each other, are —CF$_3$ or C$_2$F$_5$, and r is an integer; said perfluoropolyether when $$\begin{array}{c} \text{CFCF}_2\text{O} \\ | \\ \text{CF}_3 \end{array}$$

units are present show a kinematic viscosity lower than 8.5 cSt at 20° C. and a distillation loss not higher than 10% by weight of the total at 140° C. under atmospheric pressure and at least 90% at 260° C., whereas when $$\begin{array}{c} \text{CFCF}_2\text{O} \\ | \\ \text{CF}_3 \end{array}$$

units are absent show a kinematic viscosity lower than 18 cSt and a distillation loss not higher than 10% at 140° C. and at least 90% at 280° C.

(B) extracting the sample from the perfluoropolyether of operation (A) and dipping it into a second liquid consisting of the same perfluoropolyether as in operation (A) at a temperature between 125° and 210° C.

* * * * *